(12) United States Patent
Hishida

(10) Patent No.: US 8,409,598 B2
(45) Date of Patent: Apr. 2, 2013

(54) COPPER ION-PRODUCING COMPOSITION

(76) Inventor: Iwao Hishida, Toyonaka (JP)

( * ) Notice: Subject to any disclaimer, the term of this patent is extended or adjusted under 35 U.S.C. 154(b) by 2301 days.

(21) Appl. No.: 11/372,103

(22) Filed: Mar. 10, 2006

(65) Prior Publication Data

US 2007/0065519 A1 Mar. 22, 2007

(30) Foreign Application Priority Data

Sep. 22, 2005 (JP) ................................ 2005-276608

(51) Int. Cl.
*A01N 25/26* (2006.01)
*A01N 59/16* (2006.01)
*A01N 59/20* (2006.01)
*A01N 25/00* (2006.01)
*A01N 25/12* (2006.01)
*A01N 25/30* (2006.01)

(52) U.S. Cl. ........ 424/419; 424/617; 424/630; 424/638; 424/641; 424/646; 514/782

(58) Field of Classification Search .................. 424/419, 424/617, 630
See application file for complete search history.

(56) References Cited

U.S. PATENT DOCUMENTS

| 2,587,267 | A | * | 2/1952 | Wray et al. | .................. | 106/223 |
| 3,532,528 | A | * | 10/1970 | Bradshaw et al. | ............ | 106/403 |
| 4,086,297 | A | * | 4/1978 | Rei et al. | ...................... | 524/330 |
| 5,185,415 | A | * | 2/1993 | Kawabata et al. | ............ | 526/265 |
| 5,668,084 | A | * | 9/1997 | Unhoch et al. | ................ | 504/158 |
| 6,294,186 | B1 | * | 9/2001 | Beerse et al. | ................. | 424/405 |
| 2002/0110575 | A1 | * | 8/2002 | Gavin et al. | ................... | 424/408 |

FOREIGN PATENT DOCUMENTS

| EP | 1647345 A1 | * | 4/2006 |
| JP | 61031454 A | * | 2/1986 |
| JP | 2002035594 A | * | 2/2002 |
| WO | WO 2005007328 A1 | * | 1/2005 |
| WO | WO 2005080030 A2 | * | 9/2005 |

* cited by examiner

*Primary Examiner* — John Pak
*Assistant Examiner* — Nathan W Schlientz
(74) *Attorney, Agent, or Firm* — Kratz, Quintos & Hanson, LLP

(57) ABSTRACT

It is an object of the present invention to provide a copper ion-producing composition that has a copper ion (mineral)-based germicidal activity against *Legionella* spp., *Escherichia coli, Staphylococcus aureus*, and saprophytic bacteria occurring in the water in drinking water storage tanks, hot springs, bathhouses, and pools, and that can supply mineral, and also to provide a granular composition that contains this copper ion-producing composition. The copper ion-producing composition is obtained by mixing 0.3 to 10 weight parts surfactant with 100 weight parts metallic copper powder. The granular composition is obtained by kneading this copper ion-producing composition with poorly water-soluble material that has a softening point of not less than 70° C. The granular composition is also obtained by coating the copper ion-producing composition on the surface of poorly water-soluble material that has a softening point of not less than 70° C.

2 Claims, No Drawings

COPPER ION-PRODUCING COMPOSITION

BACKGROUND OF THE INVENTION

1. Field of the Invention

This invention relates to a copper ion-producing composition and more particularly relates to a copper-ion producing composition capable of the long-term inhibition of the proliferation of saprophytic bacteria and harmful bacteria in, for example, drinking water tanks, hot springs, bathhouses, and pools. This invention also relates to a granular composition that contains this copper-ion producing composition.

2. Description of the Related Art

The growth of, for example, *Legionella* and food-poisoning bacteria in large amounts in pools, bathhouses, hot springs, and drinking water tanks, for example, roof-top drinking water tanks, has become a major contemporary social issue and is frequently the subject of coverage in newspapers and on the television.

Within the realm of countermeasures, only chlorine is currently recognized by public agencies as a germicide for application in water, and the obligation to add a chlorine-type treatment agent, for example, hypochlorite, is becoming increasingly widespread. Several chlorine-type treatment agents are known (Japanese Registered Utility Model No. 3,040,613). With regard to the use of such chlorine-type treatment agents, it is directed pursuant to the Public Bathhouse Law that the chlorine level be maintained at 0.4 ppm and specifically that checking be carried out every 2 hours with make-up of any deficit (Revision of 25 Nov. 1993, Notice 222, Chief of the Guidance Division, Environmental Health Bureau, Ministry of Health and Welfare).

However, human health issues are known to be associated with the continuous use of chlorine, such as the production of toxic trihalomethanes, the chlorine odor, and damage to the skin and hair.

In addition, the effective chlorine in water is continually consumed by reaction with contaminants or by decomposition by ultraviolet radiation. In order to maintain the above-referenced concentration, this necessitates the rather cumbersome procedure of regularly adding chlorine on a prescribed time interval while taking precautions that its concentration does not become too high.

SUMMARY OF THE INVENTION

In view of the circumstances described above, the invention therefore pursued the development of a germicide that can substitute for chlorine, is not harmful for the human body, and is also safe for the environment and perfected a non-chlorine composition as a result.

Specifically, an object of this invention is to provide a copper ion-producing composition that has a copper ion (mineral)-based germicidal activity against *Legionella* spp., *Escherichia coli, Staphylococcus aureus*, and saprophytic bacteria occurring in the water in drinking water storage tanks, hot springs, bathhouses, and pools, and that can supply mineral. An additional object of this invention is to provide a granular composition that contains this copper ion-producing composition.

More specifically, the essential subject matter of the present invention relates to (1) a copper ion-producing composition, which is obtained by mixing 0.3 to 10 weight parts surfactant with 100 weight parts metallic copper powder;

(2) the copper ion-producing composition of (1), wherein the surface of the metallic copper powder is coated with the surfactant;

(3) the copper ion-producing composition of (1) or (2), which is obtained by mixing 10 to 500 weight parts acidic compound with 100 weight parts metallic copper powder;

(4) a granular composition, which is obtained by kneading poorly water-soluble material with a softening point of not less than 70° C. with the copper ion-producing composition according to any of (1) to (3); and (5) a granular composition, wherein the surface of poorly water-soluble material with a softening point of not less than 70° C. is coated with the copper ion-producing composition according to any of (1) to (3).

Use of the copper ion-producing composition according to the present invention achieves the excellent effects of making possible a long-term inhibition of the growth of *Legionella* ssp., *Escherichia coli, Staphylococcus aureus*, and saprophytic bacteria in the water in, for example, drinking water storage tanks, hot springs, bathhouses, and pools and of also enabling the feed of mineral into this water.

DETAILED DESCRIPTION OF THE INVENTION

The copper ion-producing composition according to the present invention comprises the mixture of 0.3 to 10 weight parts surfactant in 100 weight parts metallic copper powder.

The copper ion-producing composition according to the present invention uses metallic copper powder.

Copper is present in varying amounts in foods and is an essential metal for humans. The daily requirement is reported to be 0.6 to 2.0 mg for adults and 1.0 to 2.0 mg for children. The addition of copper mineral to infant dairy products is also recommended by the Food and Agriculture Organization (FAO) of the United Nations and by the World Health Organization (WHO). However, metallic copper, while not being harmful to the human body, undergoes almost no uptake by the human body as copper mineral even when directly ingested.

This invention was achieved based on the surprising discovery that the level of copper ion production can be substantially increased by a composition obtained by treating the surface of metallic copper powder with a specific quantity of surfactant and also by this composition containing a specific quantity of a water-soluble acidic material as described below.

The metallic copper powder used by the present invention is a finely divided powder with an average particle size of not more than approximately 40 microns.

Although finer powders are desirable for the present invention, powder that completely passes about 325 mesh is preferred from the standpoint of enabling safe production.

The grinding of metallic copper using a stone mill is an example of a method for producing metallic copper powder with the desired average particle size.

An example of the metallic copper is the mixture (copper purity of 98%) of 98 weight % copper and 2 weight % stearic acid introduced as an explosion-inhibiting lubricant.

The surfactant used by the present invention can be an anionic surfactant, cationic surfactant, amphoteric surfactant, or nonionic hydrophilic surfactant. Nonionic surfactants are preferred thereamong, and those with an HLB of 10 to 20 and particularly 13 to 15 are more preferred. Two or more surfactants may be used for this surfactant.

The surfactant is present in the copper ion-producing composition at 0.3 to 10 weight parts per 100 weight parts metallic copper powder. At less than 0.3 weight part there is insufficient surfactant to wet the entire copper powder interface, while at more than 10 weight parts the excess at the surface causes an unacceptable stickiness to occur. The preferred surfactant quantity is 3 to 6 weight parts.

In order to raise the affinity of the surface of the metallic copper for water and thereby enable high levels of ion production, the surface of the metallic copper powder is preferably treated with the surfactant in the present invention. The treatment method should be a method that effects contact between the surfactant and metallic copper powder, but is not specifically limited and can be exemplified by methods in which the two are mixed.

High levels of copper ion production can be achieved by the additional presence of a specific amount of a water-soluble acidic material in the copper ion-producing composition according to the present invention. This has the advantage of efficiently removing *Legionella* and saprophytic bacteria present in the water.

The acidic compounds used by the present invention can be exemplified by ammonium sulfate, benzoic acid, salicylic acid, tartaric acid, 2-acrylamido-2-methylpropanesulfonic acid, sodium acid metaphosphate, ferric sulfate, and methanesulfonic acid. Two or more of these acidic compounds may be used. There is a tendency for weakly acidic compounds to exhibit their effect at larger additions and for strongly acidic compounds to exhibit their effect at smaller additions.

The amount of acidic compound in the copper ion-producing composition is, in each case per 100 weight parts of the metallic copper powder, preferably 10 to 4000 weight parts, more preferably 10 to 500 weight parts, and even more preferably 80 to 300 weight parts.

A production method based on incorporation by kneading is preferably used when the acidic compound is added at about 500 to 4000 weight parts per 100 weight parts of the metallic copper powder. There is a tendency for there to be no significant difference in the degree of improvement in the effect at amounts in excess of 500 weight parts.

The copper ion-producing composition containing both metallic copper powder and acidic compound in the quantities specified hereinabove is also very suitable for use.

The copper ion-producing composition according to the present invention can be produced, for example, by mixing the metallic copper powder and surfactant and optionally the acidic compound in the quantities specified hereinabove. There are no particular limitations on the method of mixing.

While the addition of other optional components to the copper ion-producing composition is unnecessary, a silver ion-producing material may also be incorporated. The quantity of this silver ion-producing material is not particularly limited as long as the quantity thereof does not impair the activity of the copper ion-producing material.

The granular composition according to the present invention is obtained by kneading the hereinabove-described copper ion-producing composition with a poorly water-soluble material with a softening point of not less than 70° C. (also denoted below simply as the poorly water-soluble material), or by coating the copper ion-producing composition on the surface of poorly water-soluble material with a softening point of not less than 70° C. Several desirable effects advantageously accrue by preparatorily introducing this granular composition into, for example, a package or container and sinking it in the water, i.e., even upon introduction into the water, floating on the water and/or sinking with the generation of turbidity are inhibited, as is washout.

The granular composition according to the present invention can be prepared, for example, by kneading the subject copper ion-producing composition with a melt of the poorly water-soluble material generated by heating and then making the granulate, or by kneading the copper ion-producing composition with the poorly water-soluble material dissolved in solvent and then grinding after cooling or drying.

In accordance with a different method, the granular composition according to the present invention can be obtained by coating the subject copper ion-producing composition on the surface of the poorly water-soluble material with a softening point of at least 70° C.

Here, coating denotes covering, and the granular composition can be prepared, for example, by fixing the copper ion-producing composition with an adhesive to the surface of the solid poorly water-soluble material.

The copper ion-producing composition can be employed in the form of the composition or can be employed by separately mixing the individual components of the composition with the poorly water-soluble material.

With regard to the quantity of metallic copper powder in the granular composition, there is a saturation point in the quantity of copper ion release and the copper ion-producing composition need not be used in excess of this. In specific terms, 0.1 to 5 weight % is preferred for the quantity of metallic copper powder and 1 to 3 weight % is more preferred. The ionized concentration becomes inadequate at less than 0.1 weight %, while at above 5 weight % an unnecessary amount of ion is released in terms of the germicidal activity that is the objective.

The quantity of the copper ion-producing composition in the granular composition according to the present invention should therefore be adjusted so as to bring the amount of metallic copper powder into the range provided above; for example, 0.1 to 5 weight % is preferred and 0.5 to 3 weight % is more preferred.

The poorly water-soluble material used by the present invention is advantageously a poorly water-soluble material with a softening point of not less than 70° C., among which materials those that are insoluble in water and have a softening point of not less than 70° C. are preferred for their strong suitability for use in hot springs and bathhouses.

This poorly water-soluble material can be exemplified by thermoplastic resins such as ionomers, acrylonitrile-butadiene-styrene resins (ABS), ethylene-vinyl acetate copolymer resins (EVA), low-melting ethylene-tetrafluoroethylene copolymers (LMETPE), peroxyacyl nitrate (PAN), polyacetal resins (POM), polyamides (PA), polyethylenes (PE), polycarbonates, polyvinyl alcohols (PVA), polyvinyl butyral (PVB), PVF, elastomers, butadienes, polypropylenes (PP), and polymethylpentenes (TPX); as well as polyurethanes, maleic acid resins, epoxies, and polyester resins. Other examples are natural high molecular weight acetate plastics, polyterpenes, shellac, dammar gum, and rosin. Additional examples are low molecular weight polyethylenes, polypropylene resins, coumarone plastics, petroleum resins, and DCPD resins. A single such substrate or a combination of these substrates can be used.

The temperature for dissolution of the poorly water-soluble material is advantageously ambient temperature.

The solvent used to dissolve the poorly water-soluble material can be exemplified by toluene, xylene, and methylene chloride. The solvent is used in an amount capable of dissolving the poorly water-soluble material, but the amount of solvent is not otherwise limited. These solvents can be removed by drying.

The amount of poorly water-soluble material in the subject granular composition cannot be unconditionally specified since this amount varies as a function of the quantity of addition of the composition used.

For example, for the kneaded article the poorly water-soluble material is desirably used at about 30 to 70 weight % and preferably about 50 to 60 weight %, while for the coated article the poorly water-soluble material is desirably used at about 95 weight %.

In addition to the resins cited above, wood flour or an inorganic material such as glass beads, white marble, or sand can also be employed as the poorly water-soluble material used for the coated article.

The adhesive can be, for example, EVA, PVA, or RB dissolved in solvent. Those adhesives in general use can also be used, excluding water-soluble materials.

The quantity of the adhesive is not particularly limited.

The granular composition under consideration preferably contains an inorganic metal powder such as zinc oxide, iron oxide, titanium oxide, or iron powder. The presence of this inorganic metal powder in the granular composition raises the specific gravity of the granular composition, causing the granular composition to sediment in water and become a sunken material.

Kneading this inorganic metal powder into the resin or binder also offers the advantage of coarsening the consistency of the binder, raising the degree of contact between the water and copper surface, and thereby facilitating the production of copper ion.

The content of this inorganic metal powder in the subject granular composition is preferably 10 to 40 weight % and more preferably 20 to 30 weight %.

The binder is, for example, a resin in the case of kneading or an agent that acts as an adhesive during coating. More specifically, the binder is an agent that is used, together with adhesive or coating agent, e.g., resin for knead-in, to solidify the metallic copper powder and additives. With regard to its quantity, the resin fraction in the coating agent is desirably about 0.2 to 1 weight % in the composition.

The binder is preferably a foam in the present invention because this has the advantage of further raising the amount of ion production.

Conversion into the foam can be carried out, for example, by using a blowing agent such as azodicarbonamide, azobisisobutyronitrile, potassium hydrogen tartrate, or sodium bicarbonate.

The nonionic surfactant is preferably a polyoxyethylene/higher alcohol ether.

The granular composition according to the present invention with the hereinabove-described structure can make equipment and expenditures of time and effort unnecessary, in general by simply submerging a prescribed required amount by introducing a bag or container of the composition into the water in a hot springs, bathhouse, pool, or drinking water tank and replacing about every six months.

Another significant aspect of the granular composition according to the present invention is that it can be used to replace the sand filter media in the filters of water purification devices.

In addition, the use of copper-ionized water afforded by the introduction of the granular composition according to the present invention into, for example, tap water, to clean cut vegetables not only is very efficacious for vegetable disinfection, but also has the advantages of providing copper mineral-enriched vegetables and enabling preservation of the freshness.

EXAMPLES

Example 1

Preparation of Sample 1

| metallic copper powder | 1.5 weight % |
|---|---|
| EVA resin | 98.5 weight % |

These two components were mixed with a Henschel mixer and were then heated (100 to 130° C.), kneaded, and extruded with an extruder to give pellets. This was designated sample 1 (comparative article).

One weight part of sample 1 was mixed into 100 weight parts tap water and the copper ion concentration therein was measured using the EPA absorption method (Japan Ion Corporation). The results are given in Table 1.

TABLE 1

| | | copper ion concentration (ppm) | | | |
|---|---|---|---|---|---|
| sample | concentration (w/w %) | 6 hours | 15 hours | 24 hours | 48 hours |
| sample 1 | 1% | 0.03 | 0.03 | 0.03 | 0.02 |

Preparation of Sample 2

| metallic copper powder:nonionic surfactant (95:5 (weight ratio)) | 1.5% |
|---|---|
| EVA resin | 98.5% |

These two components were mixed and sample 2 (article according to the invention) was obtained by pelletization with an extruder in the same manner as for sample 1.

The copper ion concentration (ppm) was measured by the same method as for sample 1. The results are given in Table 2.

The components used in this example were as follows (also applies below).

metallic copper powder: first-grade copper powder from Hayashi Pure Chemical Ind., Ltd., average particle size of 325 mesh (complete pass through)

nonionic surfactant: Emulgen 709 from Kao Corp.

TABLE 2

| | | copper ion concentration (ppm) | | |
|---|---|---|---|---|
| sample | concentration (w/w %) | 30 minutes | 1 hour | 6 hours |
| sample 2 | 1% | 0.84 | 1.18 | 2.07 |

The results in Tables 1 and 2 demonstrate that sample 2 (article according to the invention) provided copper ion release over time in comparison to sample 1 (comparative article that used simple metallic copper powder).

Example 2

TABLE 3

|  | A | B | C |
|---|---|---|---|
| copper powder 95:5 nonionic surfactant, surface-treated product | 1.5% | 1.5% | 1.5% |
| ammonium sulfate 90:10 ST-Zn, surface-treated product | 15% | 30% | 40% |
| Zn oxide 90:10 ST-Zn, surface-treated product | 43.5% | 28.5% | 13.5% |
| EVA resin | 40% | 40% | 40% |

Samples A, B, and C were obtained by mixing the four components shown in Table 3 in the indicated concentrations with a Henschel mixer, followed by heating (extruder temperature: 100 to 130° C.), kneading, extrusion, and pelletization with an extruder.

The zinc oxide (Zn oxide) was incorporated in order to raise the specific gravity and sink the disinfectant in water.

The "copper powder 95:5 nonionic surfactant, surface-treated product" was obtained by mixing the metallic copper powder with the nonionic surfactant at a weight ratio of 95:5.

The "ammonium sulfate 90:10 ST-Zn, surface-treated product" was obtained by mixing the ammonium sulfate and zinc stearate (ST-Zn) at a weight ratio of 90:10.

The "Zn oxide 90:10 ST-Zn, surface-treated product" was obtained by mixing the zinc oxide and ST-Zn at a 90:10 weight ratio.

Samples A, B, and C were introduced into tap water at 0.2 weight % or 0.5 weight % and the time course of the copper ion concentration (ppm) was measured using a measurement instrument (from Japan Ion Corporation) that employed the EPA absorption method. In each case the copper ion concentration rose over an extended period of time of 24 hours (however, no measurements were taken at 0.5 weight % at or beyond 1 hour). The results are given in Table 4.

TABLE 4

|  |  | 1 min. | 3 min. | 5 min. | 1 hr. | 3 hr. | 6 hr. | 24 hr. |
|---|---|---|---|---|---|---|---|---|
| A | 0.2% | 0.23 | 0.27 | 0.32 | 1.97 | 2.36 | 2.54 | 3.42 |
|   | 0.5% | 0.46 | 0.67 | 0.87 | — | — | — | — |
| B | 0.2% | 0.36 | 0.51 | 0.56 | 2.84 | 3.13 | 3.13 | 3.45 |
|   | 0.5% | 1.19 | 1.49 | 1.55 | — | — | — | — |
| C | 0.2% | 0.38 | 0.49 | 0.56 | 2.28 | 2.75 | 2.85 | 3.90 |
|   | 0.5% | 0.98 | 1.15 | 1.38 | — | — | — | — | copper ion concentration: ppm

Example 3

Variation in the Copper Ion Concentration

Sample B was introduced into tap water at 0.2 weight %, after which the water was changed daily on a 24-hour cycle. The time course of the copper ion concentration was measured up to day 90 using a measurement instrument (from Japan Ion Corporation) that employed the EPA absorption method. The results are given in Table 5.

TABLE 5

| | copper ion concentration: ppm | | | | |
|---|---|---|---|---|---|
|  | 24 hours | after 15 days | after 30 days | after 60 days | after 90 days |
| sample, 0.2% | 2.84 | 2.67 | 3.13 | 3.24 | 2.40 |

The results in Table 5 show that sample B retained the capacity to release copper ion even after 90 days.

Example 4

TABLE 6

| components in the test product | sample a | sample b | sample c |
|---|---|---|---|
| EVA resin | 100 | 100 | 100 |
| copper powder (95:5 nonionic surfactant treated) | 1 | 1 | 1 |
| acidic component (90:10 ST-Zn treated) | 1 | 2 | 3 |
| adhesive (RB 1:6 toluene solution) | 2 | 4.5 | 6 |

Samples a, b, and c were prepared by mixing the individual components with a Henschel mixer to give the compositions shown in Table 6, followed by drying to remove the toluene solvent present in the adhesive.

Samples a, b, and c are granular compositions in which a metallic copper powder blend is coated and fixed on the surface of EVA resin pellets.

The acidic components used are given in the following Table 7.

TABLE 7

|  | pH |
|---|---|
| A. ammonium sulfate | 5.3 |
| B. benzoic acid | — |
| C. salicylic acid | — |
| D. tartaric acid | 2.13 |
| E. 2-acrylamido-2-methylpropanesulfonic acid | 1.4 |
| F. sodium acid metaphosphate | 1.8 |
| G. ferric sulfate | 1.8 |

Using a measurement instrument (from Japan Ion Corporation) that employed the EPA absorption method, the time course of the copper ion concentration was measured as described below for the granular compositions thus prepared.

Measurement of the copper ion concentration

For each of samples a, b, and c, test liquids were prepared by mixing in the following proportions.

0.2 w/w %: 1 g sample+499 g tap water 0.4 w/w %: 2 g sample+498 g tap water

The copper ion concentration was measured at 30 minutes and 3 hours after preparation. The results are shown in Table 8.

TABLE 8

| acidic component | 1% Cu % acidic component ratio | 0.2 w/w % 30 min.* | 3 hr.* | 0.4 w/w % 30 min.* | 3 hr.* |
|---|---|---|---|---|---|
| ammonium sulfate | 1 | 0.08 | 0.12 | 0.14 | 0.18 |
|  | 2 | 0.11 | 0.13 | 0.20 | 0.24 |
|  | 3 | 0.11 | 0.15 | 0.31 | 0.34 |
| benzoic acid | 1 | 0.09 | 0.11 | 0.18 | 0.26 |
|  | 2 | 0.13 | 0.21 | 0.29 | 0.41 |
|  | 3 | 0.28 | 0.39 | 0.48 | 0.70 |
| salicylic acid | 1 | 0.19 | 0.22 | 0.40 | 0.54 |
|  | 2 | 0.26 | 0.34 | 0.46 | 0.66 |
|  | 3 | 0.25 | 0.39 | 0.49 | 0.81 |
| tartaric acid | 1 | 0.74 | 0.84 | 1.52 | 1.75 |
|  | 2 | 1.07 | 1.26 | 2.37 | 2.97 |
|  | 3 | 1.15 | 1.44 | 2.77 | 4.63 |
| 2-acrylamido-2-methylpropanesulfonic acid | 1 | 1.68 | 1.66 | 3.53 | 3.28 |
|  | 2 | 3.18 | 3.03 | 5.46 | 5.26 |
|  | 3 | 2.29 | 2.29 | 4.25 | 3.97 |
| sodium acid metaphosphate | 1 | 1.09 | 1.23 | 1.97 | 2.19 |
|  | 2 | 3.51 | 3.83 | 3.93 | 4.20 |
|  | 3 | 2.32 | 2.48 | 6.78 | 7.66 |
| ferric sulfate | 1 | 1.49 | 1.49 | 3.02 | 2.95 |
|  | 2 | 2.59 | 2.54 | 3.80 | 3.86 |
|  | 3 | 3.35 | 3.39 | 7.60 | 7.66 |

*copper ion concentration: ppm

The results in Table 8 demonstrate long-term maintenance of the copper ion concentration for all acidic components used.

Comparative Example 1

The antimicrobial activity was tested using the conditions and procedures given below. The obtained results are given in Table 9.

Test of Germicidal Activity
1. Test sample: sample 1
2. Test organisms:
1) *Escherichia coli* (clinical isolate)
2) *Staphylococcus aureus* (clinical isolate)
3) *Legionella pneumophila* (environmental isolate)
3. Media used
A standard agar medium (Eiken Chemical Co., Ltd.) was used for 1) and 2).
WYO-α agar medium (Eiken Chemical Co., Ltd.) was used for 3).
4. Procedure
The bacteria and sample 1 were introduced simultaneously into purified water or a pH 9 solution. This was followed by gentle mixing and then standing at quiescence. The cell population was counted after 24 hours and 48 hours in order to determine bacterial survival.

TABLE 9

|  | initial | after 24 hours | after 48 hours |
|---|---|---|---|
| sample concentration: 1 w/v % | | | |
| *Escherichia coli* | $4.5 \times 10^6$ | $1.1 \times 10^5$ | $9.9 \times 10^4$ |
| *Staphylococcus aureus* | $1.1 \times 10^7$ | $3.5 \times 10^5$ | $1.9 \times 10^5$ |
| *Legionella pneumophila* | $4.7 \times 10^5$ | $9.9 \times 10^4$ | $6.7 \times 10^4$ |

TABLE 9-continued

|  | initial | after 24 hours | after 48 hours |
|---|---|---|---|
| sample concentration: 0.5 w/v % | | | |
| *Escherichia coli* | $4.5 \times 10^6$ | $4.6 \times 10^4$ | $5.5 \times 10^4$ |
| *Staphylococcus aureus* | $1.1 \times 10^7$ | $4.1 \times 10^5$ | $2.3 \times 10^5$ |
| *Legionella pneumophila* | $4.7 \times 10^5$ | $6.9 \times 10^4$ | $5.9 \times 10^4$ |

The results in Table 9 demonstrate that metallic copper on its own does not have a germicidal effect for these bacteria.

Comparative Example 2

Sodium hypochlorite was introduced into 42° C. hot water to give a chlorine level of 0.4 ppm and the time course of the residual concentration in the water was measured.

The concentration was 0.3 ppm after 30 minutes, 0.2 ppm after 60 minutes, and 0 ppm at 90 minutes. The two-hour maintenance of 0.4 ppm was therefore impossible.

Germicidal testing was also carried out at a concentration of 0.4 ppm on *Legionella* ssp., *Escherichia coli*, and *Staphylococcus aureus*, but no germicidal activity for any of these bacteria was found.

The chlorine concentration was measured using an NAT2001-CL Digital Residual Chlorine Meter from Simple Environmental Measurement Technology Laboratory.

Example 1

The antimicrobial activity was tested using the following conditions and procedures. The obtained results are shown in Table 10.

Test of Antimicrobial Activity
1. Test sample: sample 2
2. Test objective
To test the sample's antimicrobial activity for bacteria.
3. Outline of test
A bacterial solution of *Legionella pneumophila*, *Pseudomonas seruginosa*, and *Staphylococcus aureus* to which 1% sample had been added (denoted below as the test solution) was held at 25° C. and the viable count in the test solution was measured after 4 and 6 hours for the *Legionella pneumophila* and after 3, 4, 5, 6, and 24 hours for the *Pseudomonas seruginosa* and *Staphylococcus aureus*.
4. Test method
1) Test strains
*Legionella pneumophila* GIFU 9134
*Pseudomonas seruginosa* IFO 13275
*Staphylococcus aureus* IFO 12732
2) Preparation of bacterial test solutions
*Legionella pneumophila*
The test strain was cultured for 3 to 4 days at 35° C. on B-CYEα agar medium (Eiken Chemical Co., Ltd.) followed by suspension of the cells in phosphate buffer solution and adjustment of the cell count to about $10^5$/mL.
*Pseudomonas seruginosa* and *Staphylococcus aureus*
The test strain was cultured for 18 to 24 hours at 35° C. on nutrient agar medium (Eiken Chemical Co., Ltd.) followed by suspension of the cells in phosphate buffer solution and adjustment of the cell count to about $10^5$/mL.

3) Cell count measurement media and incubation conditions

Legionella pneumophila
  B-CYEα agar medium, plate spread incubation method (35° C., 5 days)
Pseudomonas seruginosa and Staphylococcus aureus
  SCDLP agar medium (Nihon Pharmaceutical Co., Ltd.), pour plate incubation method (35° C., 2 days)

4) Test procedure
  The test solution was prepared by adding 2 g of the sample to 200 mL of the particular bacterial test solution.
  The test solution was held at 25° C. and the viable count in the test solution was determined on the cell count measurement medium after holding for 4 and 6 hours in the case of Legionella pneumophila and after holding for 3, 4, 5, 6, and 24 hours in the case of Pseudomonas seruginosa and Staphylococcus aureus.
  For the control, the same test was carried out using a test solution to which the sample was not added. However, the viable count was measured at the start of the holding period for the control.

TABLE 10

Results of measurement of the viable count per 1 mL test solution

| test bacteria | measurement | addition of sample | control |
|---|---|---|---|
| Legionella pneumophila | start 25° C. | ... | $5.2 \times 10^5$ |
| | after 4 hours | 40 | $4.2 \times 10^5$ |
| | after 6 hours | <10 | $5.1 \times 10^5$ |
| Pseudomonas seruginosa | start 25° C. | ... | $2.7 \times 10^5$ |
| | after 3 hours | $1.2 \times 10^2$ | $2.0 \times 10^5$ |
| | after 4 hours | <1 | $2.2 \times 10^5$ |
| | after 5 hours | <1 | $3.2 \times 10^5$ |
| | after 6 hours | <1 | $3.6 \times 10^5$ |
| | after 24 hours | <1 | $1.2 \times 10^5$ |
| Staphylococcus aureus | start 25° C. | ... | $6.9 \times 10^5$ |
| | after 3 hours | $1.2 \times 10^5$ | $5.6 \times 10^5$ |
| | after 4 hours | $1.5 \times 10^3$ | $4.8 \times 10^5$ |
| | after 5 hours | 16 | $7.4 \times 10^5$ |
| | after 6 hours | <1 | $9.6 \times 10^5$ |
| | after 24 hours | <1 | $9.4 \times 10^5$ | control: sample was not added
... : the test was not carried out
<10, <1: not detected The results in Table 10 demonstrate that sample 2, an article according to the invention, exhibits antimicrobial activity for various bacteria. In contrast to the chlorine-containing compound of Comparative Example 2, it is also demonstrated that the antimicrobial activity was elevated over time without the repeated addition of sample.

Example 2

The antimicrobial activity was tested using the conditions and procedures given below. The obtained results are given in Table 11.
Test of Bactericidal Activity
1. Test sample: sample 3
2. Test organisms:
1) Escherichia coli (clinical isolate)
2) Staphylococcus aureus (clinical isolate)
3) Legionella pneumophila (environmental isolate)
3. Media used
A standard agar medium (Eiken Chemical Co., Ltd.) was used for 1) and 2).
WYO-α agar medium (Eiken Chemical Co., Ltd.) was used for 3)
4. Procedure
The bacteria were introduced simultaneously into water.
This was followed by gentle mixing and then standing at quiescence.
The cell population was counted after 6, 12, and 24 hours in order to determine bacterial survival.

TABLE 11

| | initial | after 6 hours | after 12 hours | after 24 hours |
|---|---|---|---|---|
| sample concentration: 0.2 w/v % | | | | |
| Escherichia coli | $1.1 \times 10^6$ | 0 | 0 | 0 |
| Staphylococcus aureus | $5.6 \times 10^6$ | 0 | 0 | 0 |
| Legionella pneumophila | $7.9 \times 10^6$ | 0 | 0 | 0 |
| sample concentration: 0.5 w/v % | | | | |
| Escherichia coli | $1.1 \times 10^6$ | 0 | 0 | 0 |
| Staphylococcus aureus | $5.6 \times 10^6$ | 0 | 0 | 0 |
| Legionella pneumophila | $7.9 \times 10^6$ | 0 | 0 | 0 |

The results in Table 11 demonstrate that, in contrast to a chlorine-based compound as in Comparative Example 2, sample 3, which is an article according to the invention, exhibits a satisfactory germicidal activity for various bacteria for 6 to 24 hours in the absence of repeated sample addition.

The copper ion-producing composition according to the present invention can be very suitably used as a germicide for saprophytic bacteria and harmful bacterial in drinking water tanks, hot springs, bathhouses, and pools.

What is claimed is:

1. A granular composition comprising a copper ion-producing composition and poorly water-soluble material, said copper ion-producing composition being obtained by mixing 0.3 to 10 weight parts surfactant with 100 weight parts metallic copper powder, treating the surface of the metallic copper powder with the surfactant, and mixing 10 to 500 weight parts acidic compound with 100 weight parts metallic copper powder,
  wherein the surface of a solid material comprising said poorly water-soluble material is coated with the copper ion-producing composition,
  wherein said granular composition further has the properties described in (a), (b), (c) and (d) below:
  (a) The metallic copper powder is a finely divided powder with an average particle size of not more than 40 microns and 0.1 to 5 weight % metallic copper powder is contained in the granular composition;
  (b) The surfactant is at least one selected from the group consisting of an anionic surfactant, cationic surfactant, amphoteric surfactant and nonionic surfactant, and those with an HLB of 10 to 20;
  (c) The acidic compound is at least one selected from the group consisting of ammonium sulfate, benzoic acid, salicylic acid, tartaric acid, 2-acrylamido-2-methylpropanesulfonic acid, sodium acid metaphosphate, ferric sulfate, and methanesulfonic acid;

(d) A substrate of the poorly water-soluble material is at least one selected from the group consisting ionomers, acrylonitrile-butadiene-styrene resins (ABS), ethylene-vinyl acetate copolymer resins (EVA), low-melting ethylene-tetrafluoroethylene copolymers (LMETPE), peroxyacyl nitrate (PAN), polyacetal resins (POM), polyamides (PA), polyethylenes (PE), polycarbonates, polyvinyl alcohols (PVA), polyvinyl butyral (PVB), PVF, elastomers, butadienes, polypropylenes (PP), polymethylpentenes (TPX), polyurethanes, maleic acid resins, epoxies, polyester resins, natural high molecular weight acetate plastics, polyterpenes, shellac, dammar gum, rosin, low molecular weight polyethylenes, polypropylene resins, coumarone plastics, petroleum resins, and DCPD resins, and the poorly water-soluble material is water-insoluble material with a softening point of not less than 70° C.

2. The granular composition of claim 1, wherein the granular composition contains at least one inorganic metal powder selected from the group consisting of zinc oxide, iron oxide, titanium oxide and iron powder.

* * * * *